United States Patent [19]

Petersen et al.

[11] Patent Number: 5,534,260

[45] Date of Patent: Jul. 9, 1996

[54] PERCUTANEOUS DRUG DELIVERY SYSTEM

[75] Inventors: Robert V. Petersen, Murray, Utah;
Tsung-Min Hsu, Union City, Calif.;
Han-Chen Lee, Salt Lake City, Utah;
Don Christy, Albany, N.Y.

[73] Assignee: University of Utah, Salt Lake City, Utah

[21] Appl. No.: 216,210

[22] Filed: Mar. 21, 1994

Related U.S. Application Data

[62] Division of Ser. No. 856,866, Mar. 24, 1992, Pat. No. 5,296,222, which is a continuation of Ser. No. 484,372, Feb. 23, 1991, abandoned, which is a continuation-in-part of Ser. No. 352,926, May 18, 1989, abandoned, which is a continuation-in-part of Ser. No. 314,819, Feb. 23, 1989, abandoned.

[51] Int. Cl.$^6$ .................................................. A61F 13/00
[52] U.S. Cl. ........................... 424/448; 514/946; 514/947
[58] Field of Search ............................ 424/448; 514/946, 514/947

[56] References Cited

U.S. PATENT DOCUMENTS

| | | | |
|---|---|---|---|
| 2,917,433 | 12/1959 | Goldman | 424/94.65 |
| 3,493,652 | 2/1970 | Hartman | 424/94.6 |
| 4,361,551 | 11/1982 | Galbraith | 424/94.2 |
| 4,567,044 | 1/1986 | DeSantis | 424/94.65 |
| 4,666,441 | 5/1987 | Andriola et al. | 424/448 |
| 4,820,720 | 4/1989 | Sanders et al. | 514/356 |
| 4,910,205 | 3/1990 | Kogan et al. | 514/290 |

FOREIGN PATENT DOCUMENTS

| | | |
|---|---|---|
| 2556218 | 6/1985 | France . |
| 8400079 | 8/1984 | WIPO . |

OTHER PUBLICATIONS

Sales Brochure for the Capital stock of Noven Pharmaceutical, Inc.

"Noven Pharmaceutical, Inc.", *Barron's*, p. 59, Sep. 19, 1988.

Package insert of Nitro–Dur (nitroglycerin) Transdermal Infusion System, Sep. 1987.

Package insert for Transderm SCOP Transdermal Therapeutic System Nov. 1985.

Package insert for the Transderm–Nitro Transdermal Drug Delivery System Jul. 1987.

*Primary Examiner*—D. Gabrielle Phelan
*Attorney, Agent, or Firm*—Trask, Britt & Rossa

[57] ABSTRACT

A percutaneous drug delivery method and enhancement composition are disclosed. The method comprises applying an enzyme preparation containing suitable amounts of non-enzyme permeation enhancers, such as lactam compounds (e.g. 1-substituted-azacycloheptan-2-one), and propylene glycol to a localized area of skin for a predetermined amount of time to enhance that area of skin's permeability to selected drug(s); occluding the area of skin during the application; and then applying the selected drug(s) to the area of skin to allow the drug to penetrate through the skin and into the circulatory system of the animal. Greatly enhanced penetration of chemicals through the skin results from the described treatment.

32 Claims, 1 Drawing Sheet

PERCUTANEOUS DRUG DELIVERY SYSTEM

RELATED APPLICATIONS

This is a division of application Ser. No. 07/856,866, filed Mar. 24, 1992, now U.S. Pat. No. 5,296,222, which is a continuation of Ser. No. 07/484,372, filed Feb. 23, 1991, now abandoned which is a continuation-in-part of U.S. Ser. No. 352,926 filed on May 18, 1989 now abandoned, which is a continuation-in-part of U.S. Ser. No. 314,819 filed on Feb. 23, 1989 now abandoned, the contents of both being incorporated herein by this reference.

BACKGROUND OF THE INVENTION

1. Field

This invention pertains to drug delivery systems generally and is more particularly directed to transdermal drug delivery systems and methods.

2. State of the Art

Devices for transdermal or percutaneous drug delivery are known in the art. Such devices include "patches" such as the Nitro-Dur® nitroglycerin transdermal infusion system marketed by Key Pharmaceutical of Kenilworth, N.J. This system consists of a "patch" containing nitroglycerin in acrylic-based polymer adhesives with a resinous crosslinking agent to provide a continuous source of nitroglycerin to the patient. The patches are available in various dosage strengths for delivering various amounts of nitroglycerin to the patient over a twenty-four hour period. These patches vary in size from five to thirty square centimeters ($cm^2$). The rated release of the drug is dependent upon the area of the patch with 0.5 milligram (mg) being released for every square centimeter of patch per 24 hours. The patch is applied to any convenient skin area, especially the arm or chest.

Another transdermal patch is marketed by Noven Pharmaceutical of Miami, Fla. The Noven patch has been used with nitroglycerin and estrogen. It consists of a non-occlusive backing layer, a drug reservoir for containing the drug, a microporous rate controlling membrane which contacts the skin of the patient, and an adhesive formulation for keeping the patch in contact with the skin. Drug passes from the reservoir through the membrane, through the patient's skin, and into the bloodstream.

Another transdermal patch, Transderm SCOP®, is used by CIBA Consumer Pharmaceutical Co. of Summit, N.J. It is a film 0.2 mm thick and 2.5 $cm^2$, with four layers. Proceeding from the visible surface towards the surface attached to the patient's skin (FIG. 1), these layers are: (a) a backing layer of tan-colored, aluminized, polyester film; (b) a drug reservoir of scopolamine, mineral oil, and polyisobutylene; (c) a microporous polypropylene membrane that controls the rate of delivery of scopolamine from the system to the skin surface; and (d) an adhesive formulation of mineral oil (12.4 mg), polyisobutylene (11.4 mg) and scopolamine (1.5 mg). A protective peel strip of siliconized polyester, which covers the adhesive layer, is removed before the system is used. The inactive components, mineral oil and polyisobutylene, are not released from the system. The system is "programmed" to deliver 0.5 mg of scopolamine at an approximately constant rate of the systemic circulation over the three-day lifetime of the system. An initial priming dose of scopolamine, released from the adhesive layer of the system is believed to saturate the skin binding sites for scopolamine and bring the plasma concentration of scopolamine to the required steady state level. A continuous controlled release of scopolamine, which flows from the drug reservoir through the rate-controlling membrane, maintains the plasma level constant.

A similar system is also used by CIBA Pharmaceutical Company in its Transderm-Nitro® nitroglycerin. In this system, the rate controlling membrane is an ethylene/vinyl acetate copolymer membrane that is permeable to nitroglycerin, and the adhesive used is a hypoallergenic silicone adhesive.

Another system to deliver drugs through the skin of a patient is disclosed in French patent 2,556,218. This patent discloses "sticks" for roll-on application of a desired drug. These sticks contain, as components, an enzymatic penetrating agent, the desired drug, and various excipients. The enzymatic penetrating agents disclosed include alpha-chymotrypsin and hyaluronidase. Drugs disclosed for use with these sticks include aspirin, lidocaine, lutadine, vitamin A, and tetracycline. Excipients disclosed include sodium glycerol stearate. The desired drug, enzymatic penetrating agent, and excipient can be mixed together to form a homogeneous mixture.

Alternatively, the various components of the stick can be separated from one another in a manner that brings one component (e.g., enzymatic penetrating agent) immediately after the other (e.g., drug) in contact with the local application zone of the patient's skin for treatment (e.g. a solid stick can make up two longitudinal or concentric parts of one stick). The enzymatic penetrating agents increase the penetration of the desired drug through the patient's skin or mucous membrane.

Another transdermal drug delivery system is disclosed in French Patent No. 2,448,903. This system consists of at least one antibiotic, an enzyme, an anti-inflammatory agent, and/or a local anesthetic agent, and/or a heteratolytic agent, and/or a mucolytic agent, and/or an emulsifying agent. Enzymes disclosed include hyaluronidase, streptokinase, streptodornase, trypsin, chymotrypsin, α-chymotrypsin; α-amylase, bromelain, papain, deoxyribonuclease, collagenase, and sutilain. This system is used to provide localized antibiotic therapy.

U.S. Pat. Nos. 3,989,816, 4,316,893, and others to Rajadhyaksha, disclose the use of lactam compounds, (e.g. 1-n-Dodecylazacycloheptan-2-one Azone™ Nelson Research & Development Company, Irvine, Calif.) for carrying physiologically active agents through the skin or other membranes of an animal or human.

The use of various penetration enhancing substances in connection with various drugs for percutaneous delivery have been disclosed in U.S. Pat. No. 4,755,535 to Minaskanian (target drug used with azacycloalkene-type substances), U.S. Pat. No. 4,699,777 to Zupon, et al. (1-dodecyl-azacycloheptan- 2-one and urea used to enhance penetration effect of albuterol), U.S. Pat. No. 4,820,711 to Pearlman (cytotoxic compounds dissolved in Azone or Azone-related compounds to relieve actinic keratosis), and U.S. Pat. No. 4,557,934 to Cooper (use of a binary mixture of Azone or Azone-related compounds and a $C_3$–$C_4$ diol to enhance penetration of various drugs).

SUMMARY OF THE INVENTION

The invention includes a percutaneous permeation enhancer which comprises a potentiating amount of an enzyme preparation in admixture with a non-enzymatic penetration enhancer, such as a lactam compound. Both the enzyme preparation and the non-enzymatic penetration enhancer are present in sufficient quantities and concentrations so that when they are applied to an area of the skin for a selected period of time, they enhance the penetration of chemical agents through the skin. "Skin", as used herein, refers to the outer body integument as well as those tissues which are histologically related, such as nails and the like.

The percutaneous permeation enhancer may further include solubilizers for assisting in the admixture of the components into a liquid solvent such as water. The enhancer may also include other chemical agents, such as propylene glycol, which enhance the penetration of a chemical agent through the skin.

Non-enzymatic penetration enhancers, for purposes of this invention, are compositions which enhance the permeation of biologically active agents (e.g. drugs) through the skin of an animal. Such compositions include alcohols, such as ethanol and isopropanol; polyols, such as n-alkanols ($C_6$–$C_8$), limonene, terpenes, dioxolane, propylene glycol, ethylene glycol, other glycols, and glycerol; sulfoxides, such as dimethylsulfoxide ("DMSO") and methyl dodecyl sulfoxide; esters such as isopropyl myristate/palmitate, ethyl acetate, butyl acetate, methyl propionate, and capric/caprylic triglycerides; ketones, such as 2-alkyl cyclohexanones, t-butyl cyclohexanones, and various $C_8$ derivatives; amides, such as acetamides; oleates, such as triolein; various surfactants, such as Brij 96, Tweens (Atlas Chemical Company), myrjs, and sodium lauryl sulfate; various alkanoic acids such as caprylic acid ($C_6$–$C_{10}$); lactam compounds, such as Azone; alkanols, such as oleyl alcohol; and admixtures thereof. These compositions are believed to enhance permeation of biologically active agents by acting at the lipid matrix of the stratum corneum (i.e. by enhanced intercellular matrix diffusion).

"Lactam compound", as used herein, is an organic compound containing the —NR—CO—group in a ring. For use in the invention, the R group of this compound should be free from the lactam ring, unlike the penicillins and cephalosporins wherein the R group is bonded to another portion of the lactam ring to form a bicylic compound. Lactam compounds useful in the invention have the following typical structural formula:

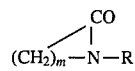

wherein R is an alkyl, aryl, or phenyl group. These compounds, as disclosed in U.S. Pat. Nos. 3,989,816 and 4,316,893 enhance the penetration of chemical agents through the skin. Similar permeation enhancing compounds are disclosed in U.S. Pat. Nos. 4,405,616; 4,415,563; 4,423,040; 4,424,210; 4,444,762; 4,525,199; 4,562,075; 4,801,586; and 4,806,341, the contents of which are incorporated by this reference. Concentrations of these agents effective to enhance the skin's permeability to drugs are disclosed throughout these patent references. A synergistic permeation enhancement effect is achieved when potentiating amount of these compounds is in admixture with an enzyme.

The percutaneous permeation enhancers of the present invention are used as an aid in delivering a drug percutaneously to an animal, including humans. The percutaneous permeation enhancer is first applied to a localized area of the skin in a sufficient quantity and concentration to enhance eventually the permeability of the skin to a drug. The enhancer is kept in contact with the skin for a sufficient amount of time to enhance the skin's permeability to the drug. The area of skin may optionally be occluded during the time in which the enhancer is in contact with the skin. The drug is then applied to the localized area of skin and permeates through the skin to be delivered to the animal.

DETAILED DESCRIPTION OF THE PREFERRED EMBODIMENTS

Figure 1:
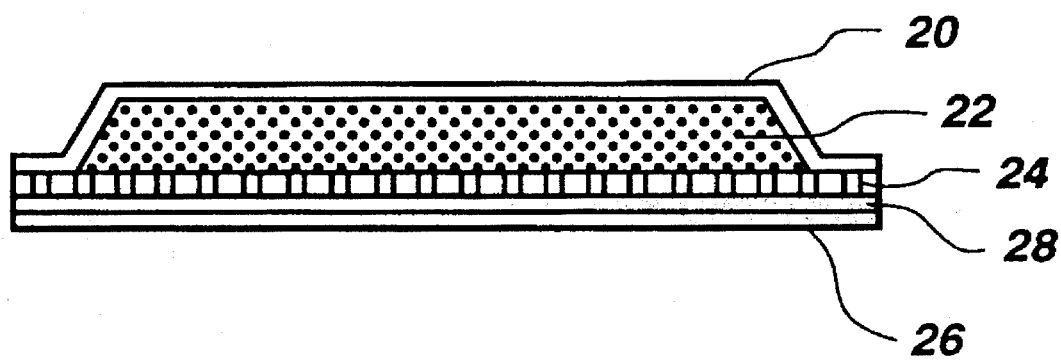
FIG. 1 stylistically depicts a side view of a prior art patch useful in the practice of the invention.

Studies indicate that the use of a proteolytic enzyme on an area of skin prior to application of a drug to the same area of skin for percutaneous absorption significantly enhances penetration of the drug through the skin. For example, there is a 3,346 percent increase in absorption of tetraethylammoniumbromide (TEAB) when the skin is pretreated with papain. (See Example I; see also, Example IV (1) and (2).) Although application of an enzyme alone is effective, increased concentrations of papain lead to increased damage to the skin and can cause bleeding. Further studies have indicated, however, that when a proteolytic enzyme is admixed with a non-enzymatic substance there is a further significant increase in penetration of the drug into the skin. Therefore, lower concentrations of papain can be used with an increase in drug absorption. Thus, the invention includes the admixture of enzyme and non-enzyme components to enhance permeation of the skin in anticipation of application of a drug.

Enzymes useful in the percutaneous permeation enhancers ("enhancers") of the present invention are enzymes capable of altering structures of the skin of the particular animal to be treated so as to enhance the skin's permeability to a selected drug or drugs. Enzymes preferred for these purposes do not substantially react detrimentally with the selected drug or non-enzymatic penetration enhancer, do not degrade substantially to an inactive state at body temperature or in solution, do not cause unacceptable discoloration or scarring of the skin, and react in sufficiently small concentrations to be useful over a relatively small area of skin. A preferred enzyme is papain, which is readily available from Sigma Chemical Company of St. Louis, Mo. or other sources.

Other enzymes useful in the practice of the invention include pancreatin (actually a mixture of enzymes), ficin, bromelain, elastase, and pepsin. Further useful enzymes include hyaluronidase, streptokinase, streptodornase, trypsin, chymotrypsin, α-chymotrypsin, α-amylase, deoxyribonuclease, collagenase, sutilain, and other specific and non-specific proteolytic enzymes. For purposes of this disclosure, a non-specific proteolytic enzyme is one that alters a protein's structure at nearly any point or level, including breaking down disulfide bonds, which can result in complete denaturation of the skin protein. A specific proteolytic enzyme, however, is one that merely alters the protein under conditions not sufficiently severe to alter protomer configuration. Papain and pancreatin, are preferred in the practice of this invention; although other proteolytic enzymes, such as bromelain and ficin, will also work.

Some enzyme preparations will also include "activating agents." These activating agents enhance the percutaneous delivery of the drug(s) through the skin. For example, papain from Sigma Chemical may be activated with the chelating agent ethylene-diaminetetraacetic acid ("EDTA") in admixture with cysteine. Such activation of papain increases the penetration of tetraethylammonium bromide (TEAB)

through the skin in comparison to use of the papain without such activation. Other possible sources of papain include papain from Allergan. Allergan papain is contained in a contact lens cleaning product (tablets for dissolution in water) wherein activators are included. Amounts of EDTA in a papain enzyme preparation will vary from 2 mg/ml to about 20 mg/ml.

An especially preferred activating agent for use with papain is 0.10 molar cysteine in combination with 0.0375 molar EDTA which activates the papain to achieve greater penetration of drug through the skin.

Whatever the enzyme or enzymes selected, each is typically admixed with a non-enzyme penetration enhancer such as a lactam compound, (e.g. Azone™), and a liquid, such as propylene glycol, to form an enhancer. The concentration of enzymes(s) in liquid will be of a sufficient quantity to increase the skin's permeability to selected drugs over a predetermined time period.

As used herein, "Azone" is 1-n-dodecylazacycloheptan-2-one, available from Nelson Research & Development Co. of Irvine, Calif. A method of preparing this compound is disclosed in U.S. Pat. No. 4,316,893 to Rajadhyaksha in Example 16 (column 11, lines 36–51), Example 10 (column 10, lines 1–19) and Example 8 (column 9, lines 10–49) the contents of which are incorporated by this reference. Concentrations of Azone ranging from about 0.5% to about 10% are useful, although 2% is preferred. All references herein to percentages in a composition are to weight percentages unless indicated otherwise.

Several other lactams which are chemically related to Azone™ may be useful in the practice of this invention. Enzymes are believed to potentiate the ability of lactam compounds to enhance percutaneous penetration of chemical agents. Lactam compounds useful in the instant invention are disclosed in the aforementioned U.S. patents especially U.S. Pat. Nos. 4,316,893 and 3,989,816 to Rajadhyaksha, the contents of which are incorporated by this reference. The preparation of some of these related lactams is disclosed in U.S. Pat. No. 4,316,893, Examples 1–23 therein.

The enzyme and lactam compound act to potentiate one another forming a synergistic effect. That is, the permeation enhancement is greater than would be anticipated from the combined individual effect of each agent (see Example III). Other non-enzyme penetration enhancers which can be used in the admixture include various alcohols, polyols, sulfoxides, esters, ketones, amides, oleates, various surfactants, alkanoic acids, and alkanols which demonstrate a capability for enhancing permeation. More than one non-enzyme enhancer may be used in combination as a penetration enhancer. As shown by Example IV, studies indicate that these other non-enzyme compounds, in admixture with an enzyme such as papain, can be very effective in increasing permeation of the skin. Those non-enzyme compounds which are water-soluble tend to be more effective in permeation potentiation than non-enzyme compounds which are emulsions. (See Example IV (8a) and (8b).) The enhancement effect of the non-enzyme component on percutaneous penetration of a drug would be expected to be merely additive. However, as illustrated by Example IV, the enhancement effect of the enzyme and non-enzyme combination causes a dramatic increase in penetration over a mere additive effect.

Preferably, the concentration of enzyme(s) in the enhancer will be great enough to increase the skin's permeability to the selected drug in less than 24 hours, for practical reasons. Concentrations of papain in water will generally be greater than about 0.019 milligrams/milliliter (mg/ml). Preferred concentrations of papain in water will be less than about 0.093 mg/ml. Pretreatment of skin samples with papain concentrations greater than 0.093 mg/ml at pH 7.4 lead to greater drug penetration, but also damage the skin, possibly leading to bleeding.

In addition to the aforementioned non-proteolytic permeation enhancers, other chemical agents which enhance permeation may also be added to the permeation enhancer admixture. Propylene glycol, for example, is a particularly preferred agent since it may also assist in solubilizing the lactam compound(s) in addition to enhancing the skin's permeability to certain drugs.

Solubilizers, such as Spans and Tweens increase the solubility of various components of the enhancers into the liquid solvent.

Ideally, the percutaneous permeation enhancers are compounded to retain stability for long periods of time. Various factors, such as composition, pH of the solution, and choice of solvent, influence the stability of an enzyme preparation. For maximum stability, when enzymes such as papain and bromelain are used, the enzyme preparation should be dissolved in water and should have a pH of from about 3 to about 10. The enhancers are also preferably refrigerated before use and kept at temperatures of 3°–5° C.

The enzyme or drug preparation may also be stabilized with various preservatives. Considerations in selecting an agent for use as a preservative in the system, as with most pharmaceutical preparations, include: a) the agent's spectrum of activity; b) the agent's stability over time; c) the agent's relative toxicity; d) the agent's allergenic potential; e) the agent's compatibility with the other constituents of the preparation, and f) the agent's odor. Various alcohols, e.g. ethanol or isopropanol, quaternary ammonium surfactants, and other compounds well known to those skilled in the art may be used as a preservative. The *United States Pharmacopeia* XXXII, page 198, contains a section on stability considerations in compounding at pages 1345 through 1347, the contents of which are incorporated by this reference.

For maximum sustained penetration of drug(s) through treated skin, the pH of the percutaneous permeation enhancer will vary from 5.8 to 8.0, with the preferred pH being about 7.4. (See Example V)

Although the concentrations of either proteolytic enzyme or enhancers may be decreased if contact time is to be increased, it is generally preferred that certain concentrations be used inasmuch as treatment time may be minimized by use of such concentrations. Long treatment times may be annoying to patients and discourage them from employing a therapeutically necessary treatment.

The enhancer preparation can be applied using any of several well-known techniques for applying a liquid to a surface. For example, a brush, swab, or spray container containing the enhancer preparation may be used to apply the preparation to the skin.

In one embodiment of the invention, the enhancer preparation is an admixture of lactam compound(s) and proteolytic enzyme(s), and the enhancer preparation is applied directly to the skin surface. In an alternative embodiment, first a lactam compound dissolved in a solvent is applied, then an enzyme preparation is applied. The order of application of non-enzymatic and enzymatic compounds can be reversed, it only being important that both the compound(s) be in contact with the same area of skin at the same time.

In a particularly preferred embodiment, the enhancement preparation is contained within a reservoir of a "patch"

which is placed on the animal's skin. As shown in FIG. 1, which is a side view of a typical patch, the patch would include a backing 20, a reservoir 22 to contain the enzyme preparation, a membrane 24 to contain and release the contents of the reservoir, and a protective peel strip 26 or strips. Patches are typically round or oblong when viewed from above, and are preferably sized to affix neatly to the animal's skin. The membrane 24 is typically rate-controlling or semi-permeable to the contents of the reservoir 22. Adhesive 28 is located around the outer circumference of the patch adjacent to the membrane 24, and a separate, removable, protective peel strip 26 is displaced over the adhesive for removal prior to applying the patch so that the patch will adhere to the animal's skin.

Adhesives are preferably hypoallergenic substances which are useful in retaining the protective peel strips to the patch and the patch to the animal's skin. Preferred adhesives include silicone adhesive formulations and other adhesives well known to those skilled in the art.

A patch is particularly preferred because the occlusion means are included as part of the system, i.e., the backing 20. Other occlusion means include aluminized plastic, plastic film such as Saran Wrap™, and Bioclusive™ tape. Important factors to consider when selecting occlusion means are a) non-reaction with the contents of the reservoir, b) adequate containment of the contents to the desired localized area of skin, and c) non-reaction with the skin to a detrimental degree. In the case of use with humans, the backing is preferably skin-colored for cosmetic reasons.

When a patch is used as part of the system, the protective peel strip is removed from the patch, and the patch is applied to the skin. The enhancement preparation permeates through the membrane, and contacts the skin. After the skin's structure has been sufficiently altered to allow enhanced passage of the selected drug through the skin, the enhancement preparation containing patch is removed.

The selected drug or drug preparation, also preferably in a liquid form, is then applied to the skin. The drug or drug preparation is then applied in a similar way as previously described for the enhancement preparation. For example, a drug may be contained within the reservoir 22 of a patch which is then applied to the same localized area of skin previously treated with the enzyme preparation. Such a reservoir would preferably contain the drug in a sufficient concentration to allow therapeutic levels of the drug to pass through the skin to the animal's circulatory system.

Selection of the drug is dependent upon the disease state and animal to be treated. Ideal drugs for percutaneous drug delivery in accordance with the invention include hormones such as progesterone; quaternary compounds such as acetylcholine; and anionic chemicals such as coumadin. Therapeutic classes of drugs for use in the system include antihypertensive agents such as beta-blockers, anti-nauseants such as chlorpromazine, and anti-arrythmics, and analgesics.

Polypeptides, such as hormones and the like, are particularly aided in percutaneous delivery by the permeation enhancer invention. Tests performed on pretreated mouse skin indicate that polypeptides of lower molecular weight, ranging from about 800 to about 15,000 in molecular weight, are successfully used in combination with an enzyme/non-enzyme enhancement compound. (See Example VI) There is some indication that polypeptides of higher molecular weight tend to be fractionated when applied to skin pretreated with papain. The exact mechanism of fractionation is unclear, but gel electrophoresis on samples of polypeptides and pure buffered solution diffused through pretreated mouse skin indicated that no endogenous protein is lost from the cells. Examples of polypeptides of lower molecular weight which can be used are insulin and synthetic growth hormones.

Where active ingredients (i.e., enzymes, lactam compounds or drugs) which are not stable in solution for sufficiently long periods of time, the enzyme, enzymes, drug or drugs can be mixed with solvent and then injected with a syringe, or otherwise introduced, into the reservoir of the patch immediately prior to the patch's application to the animal's skin.

The invention allows for the controlled and timed noninvasive release of drugs to the animal. By increasing the concentration of drug in the drug-containing patch, the amount of drug which passes through the skin can be increased and the duration of drug application increased. Furthermore the invention allows for the penetration of larger molecular weight compounds than was previously attainable.

The localized area of the skin to which the enzyme/non-enzyme compounds and drug preparations are applied is preferably a relatively thin layer of skin; other areas of typically thicker skin, such as the sole of the foot, should be avoided. Furthermore, hairy areas of skin should be avoided, or the hair should first be removed.

In one embodiment of the system, the system is present in a kit form. Included in this kit are means for applying the percutaneous permeation enhancers, occlusion means, and means for applying the selected drug. Means for applying the enhancer and selected drug may be differently marked patches, one patch containing the enzyme preparation and the other patch containing the drug. Different patch marking may include different coloration of the patches and/or the protective peel strips. All components of the kit are contained within a convenient package for use by a medical or veterinary practitioner or patient.

The kit may also include means for mixing the enzyme and non-enzyme components with solvent such as a small glass container containing a solvent selected for optimal use with the enzyme and non-enzyme components; means for mixing the selected drug(s) with solvent such as a small glass container containing a solvent selected for the drug; and means for introducing active ingredient preparations into the patches such as a needle-bearing syringe. These various means would typically be included in the kit when any, or all, active ingredients or constituents thereof are not stable for sufficient lengths of time when premixed in solution.

While not intending to be bound by one explanation of the invention, the following may be of assistance in understanding the invention.

EXAMPLE I

Enhancement Studies Using Proteolytic Enzyme Alone

Drug penetration through a skin barrier is thought to be a process of passive diffusion and may be described by Fick's First Law:

$$J = -D \frac{dC}{dX}$$

where J is the flux of a drug through a skin barrier, D is the diffusion constant of a drug in the skin barrier, and dC/dX is the concentration gradient of a drug between the vehicle and the skin barrier.

For steady state diffusion:

$$J = \frac{DK}{h} C_v = PC_v$$

where K is the partition coefficient of drug between a skin barrier and the vehicle, $C_v$ is the concentration of drug dissolved in the vehicle, h is the thickness of the skin barrier, and P is the permeability of a drug through the skin barrier.

---

Enhancement of TEAB Penetration Through Hairless
Mouse Skin Using Enzyme Component Alone

---

1. Without papain pretreatment
   $J = 2.72 \times 10^{-5}$ mg/cm$^2$/sec
   $P = 2.54 \times 10^{-8}$ cm/sec
2. Pretreated with Sigma papain of concentration 0.010
   mg/0.108 ml (0.093 mg/ml)
   $J = 6.87 \times 10^{-4}$ mg/cm$^2$/sec
   $P = 0.85 \times 10^{-6}$ cm/sec $$\text{Ratio of enhancement} = \frac{P \text{ with enhancer}}{P \text{ without enhancer}} =$$

$$\frac{0.85 \times 10^{-6}}{2.54 \times 10^{-8}} \times 100\% = 3346\%$$

3. Pretreated with Allergan papain of concentration
   0.170 mg/0.200 ml (0.850 mg/ml)
   $J = 1.04 \times 10^{-3}$ mg/cm$^2$/sec
   $P = 1.29 \times 10^{-6}$ cm/sec $$\text{Ratio of enhancement} = \frac{1.29 \times 10^{-6}}{2.54 \times 10^{-8}} \times 100\% = 5070\%$$

4. Pretreated with Sigma papain of concentration 0.170
   mg/0.602 ml (0.278 mg/ml)
   $J = 1.46 \times 10^{-3}$ mg/cm$^2$/sec
   $P = 1.81 \times 10^{-6}$ cm/sec $$\text{Ratio of enhancement} = \frac{1.81 \times 10^{-6}}{2.54 \times 10^{-8}} = 100\% = 7126\%$$

---

EXAMPLE II

Preparation of Permeation Enhancer

A percutaneous permeation enhancer having the following formula was prepared:

| Compound | Quantity |
| --- | --- |
| Papain (Allergan) | 0.0465 mg/ml |
| Azone™ | 2% |
| Propylene Glycol | 15% |
| Tween 20 | qs to solubilize Azone |
| Normal Saline Solution | qs/n ad 20 ml |

The Tween 20 was used to solubilize the Azone™ in the admixture.

EXAMPLE III

The effect of the percutaneous enhancer, as prepared in Example II above, was measured on the penetration of the quaternary compound acetylcholine chloride through hairless mouse skin at pH 7.4. The addition of Azone allowed the concentration of papain in the enhancer to be halved which minimized papain's irritating effect on the skin. The results showed that while an eighty-eight fold increase in penetration of acetylcholine chloride was obtained by papain pretreatment alone, and a seven fold increase by Azone™ and propylene glycol alone, a 110 fold increase was achieved by the use of a combination of Azone™ propylene glycol and papain. The data below indicates a potentiating or synergistic effect in combining the agents for use as an enhancer.

---

Enhancement effect of 0.0465 mg/ml Sigma papain alone and in
combination with 2% Azone™ and 15% propylene glycol on the
penetration of acetylcholine chloride through hairless mouse
skin at pH 7.4.

---

1. Pretreated with 0.0465 mg/ml papain alone.
   $J = 5.67 \times 10^{-4}$ mg/cm$^2$/sec
   $P = 2.83 \times 10^{-6}$ cm/sec
   $E = 88.4$
2. Pretreated with 2% Azone™ and 15% propylene glycol alone
   $J = 4.57 \times 10^{-5}$ mg/cm$^2$/sec
   $P = 2.29 \times 10^{-7}$ cm/sec
   $E = 7.2$
3. Pretreated with a combination of 0.0465 mg/ml sigma
   papain and 2% Azone™ and 15% propylene glycol
   $J = 7.01 \times 10^{-4}$ mg/cm$^2$/sec
   $P = 3.51 \times 10^{-6}$ cm/sec
   $E = 109.7$

---

EXAMPLE IV

---

Effect of Various Non-Enzyme Components in Admixture
With Papain on Penetration of Tetraethylammonium bromide

---

1. Results on the penetration of $^{14}$C-TEAB through normal hairless mouse skin (placebo, n = 3)
   $J = (4.02 \pm 2.13) \times 10^{-6}$ mg cm$^{-2}$s$^{-1}$
   $P = (4.95 \pm 2.62) \times 10^{-9}$ cm s$^{-1}$
2. Results on the penetration of $^{14}$C-TEAB through hairless mouse skin pretreated with 0.0465 mg/ml papain for 24 hours (n = 3)
   $J = (1.33 \pm 0.48) \times 10^{-4}$ mg cm$^{-2}$s$^{-1}$
   $P = (1.63 \pm 0.59) \times 10^{-7}$ cm s$^{-1}$
   $E = 32.93$
3a. Results on the enhancement effect of 5% Brij 96 alone on the penetration of $^{14}$C-TEAB through hairless mouse skin (n = 1)
   $J = 3.10 \times 10^{-5}$ mg cm$^{-2}$s$^{-1}$
   $P = 3.81 \times 10^{-8}$ cm s$^{-1}$
   $E = 7.70$
3b. Results on the enhancement effect of 5% Brij 96/0.0465 mg/ml papain combination on the penetration of $^{14}$C-TEAB through hairless mouse skin (n = 2)
   $J = (4.14 \pm 0.65) \times 10^{-4}$ mg cm$^{-2}$s$^{-1}$
   $P = (5.09 \pm 0.81) \times 10^{-7}$ cm s$^{-1}$
   $E = 102.83$
4a. Results on the enhancement effect of 25% EtAc/25% EtOH alone on the penetration of $^{14}$C-TEAB through hairless mouse skin (n = 1)
   $J = 3.68 \times 10^{-6}$ mg cm$^{-2}$s$^{-1}$
   $P = 4.54 \times 10^{-9}$ cm s$^{-1}$
   $E = 0.92$
4b. Results on the enhancement effect of 25% EtAc/25% EtOH/0.0465 mg/ml papain combination on the penetration of $^{14}$C-TEAB through hairless mouse skin (n = 2)
   $J = (4.34 \pm 0.01) \times 10^{-4}$ mg cm$^{-2}$s$^{-1}$
   $P = (5.34 \pm 0.01) \times 10^{-7}$ cm s$^{-1}$
   $E = 107.88$
5a. Results on the enhancement effect of 40% EtOH/10% PG alone on the penetration of $^{14}$C-TEAB through hairless mouse skin (n = 1)
   $J = 1.54 \times 10^{-5}$ mg cm$^{-2}$s$^{-1}$
   $P = 1.90 \times 10^{-8}$ cm s$^{-1}$
   $E = 3.84$
5b. Results on the enhancement effect of 40% EtOH/10% PG/0.0465 mg/ml papain combination on the penetration of $^{14}$C-TEAB through hairless mouse skin (n = 2)
   $J = (2.13 \pm 0.82) \times 10^{-4}$ mg cm$^{-2}$s$^{-1}$
   $P = (2.63 \pm 1.01) \times 10^{-7}$ cm s$^{-1}$

-continued

Effect of Various Non-Enzyme Components in Admixture
With Papain on Penetration of Tetraethylammonium bromide E = 53.13
6a. Results on the enhancement effect of 2% dioxolane alone
on the penetration of $^{14}$C-TEAB through hairless mouse
skin (n = 1)
$J = 4.23 \times 10^{-6}$ mg cm$^{-2}$s$^{-1}$
$P = 5.21 \times 10^{-9}$ cm s$^{-1}$
E = 1.05
6b. Results on the enhancement effect of 2%
dioxolane/0.0465 mg/ml papain combination on the
penetration of $^{14}$C-TEAB through hairless mouse skin
(n = 2)
$J = (1.65 \pm 1.00) \times 10^{-4}$ mg cm$^{-2}$s$^{-1}$
$P = (2.03 \pm 1.23) \times 10^{-7}$ cm s$^{-1}$
E = 41.01
7a. Results on the enhancement effect of 10%
caprylic/capric triglyceride alone on the penetration
of $^{14}$C-TEAB through hairless mouse skin (n = 1)
$J = 1.11 \times 10^{-5}$ mg cm$^{-2}$s$^{-1}$
$P = 1.37 \times 10^{-8}$ cm s$^{-1}$
E = 2.77
7b. Results on the enhancement effect of 10%
caprylic/capric triglyceride/0.0465 mg/ml papain
combination on the penetration of $^{14}$C-TEAB through
hairless mouse skin (n = 2)
$J = (1.00 \pm 0.28) \times 10^{-4}$ mg cm$^{-2}$s$^{-1}$
$P = (1.23 \pm 0.35) \times 10^{-7}$ cm s$^{-1}$
E = 24.85
8a. Results on the enhancement effect of 10% oleyl alcohol
alone on the penetration of $^{14}$C-TEAB through hairless
mouse skin (n = 1)
$J = 1.49 \times 10^{-4}$ mg cm$^{-2}$s$^{-1}$
$P = 1.83 \times 10^{-7}$ cm s$^{-1}$
E = 36.97
8b. Results on the enhancement effect of 10% oleyl
alcohol/0.0465 mg/ml papain combination on the
penetration of $^{14}$C-TEAB through hairless mouse skin
(n = 2)
$J = (1.46 \pm 0.44) \times 10^{-4}$ mg cm$^{-2}$s$^{-1}$
$P = (1.80 \pm 0.54) \times 10^{-7}$ cm s$^{-1}$
E = 36.36
9a. Results on the enhancement effect of 1% n-decyl methyl
sulfoxide alone on the penetration of $^{14}$C-TEAB through
hairless mouse skin (n = 1)
$J = 4.35 \times 10^{-6}$ mg cm$^{-2}$s$^{-1}$
$P = 5.35 \times 10^{-9}$ cm s$^{-1}$
E = 1.08
9b. Results on the enhancement effect of 1% n-decyl methyl
sulfoxide/0.0465 mg/ml papain combination on the
penetration of $^{14}$C-TEAB through hairless mouse skin
(n = 2)
$J = (1.98 \pm 0.38) \times 10^{-4}$ mg cm$^{-2}$s$^{-1}$
$P = (2.44 \pm 0.46) \times 10^{-7}$ cm s$^{-1}$
E = 49.31

EXAMPLE V

| | A. Effect of pH on drug penetration through normal untreated hairless mouse skin. | | | |
|---|---|---|---|---|
| J&P Drug | pH | | | |
| (Class) | 5.9 | 6.6 | 7.4 | 8.0 |
| Acetylcholine Chloride (quaternary) | $J = 5.83 \times 10^{-6}$ mg/cm$^2$/sec $P = 2.91 \times 10^{-8}$ cm/sec | $J = 5.21 \times 10^{-6}$ $P = 2.60 \times 10^{-8}$ | $J = 6.41 \times 10^{-6}$ $P = 3.20 \times 10^{-8}$ | $J = 9.32 \times 10^{-6}$ $P = 4.66 \times 10^{-8}$ |
| Progesterone (nonionic) | $J = 2.30 \times 10^{-7}$ mg/cm$^2$/sec $P = 2.88 \times 10^{-6}$ cm/sec | $J = 2.34 \times 10^{-7}$ $P = 2.92 \times 10^{-6}$ | $J = 2.34 \times 10^{-7}$ $P = 2.92 \times 10^{-6}$ | $P = 2.47 \times 10^{-7}$ $J = 3.09 \times 10^{-6}$ |
| Warfarin (anionic) | $J = 1.66 \times 10^{-8}$ mg/cm$^2$/sec $P = 1.66 \times 10^{-7}$ | $J = 9.16 \times 10^{-9}$ $P = 9.16 \times 10^{-8}$ | $J = 4.68 \times 10^{-9}$ $P = 4.68 \times 10^{-8}$ | $J = 4.73 \times 10^{-9}$ $J = 4.73 \times 10^{-8}$ |

-continued

| | cm/sec | | | |
|---|---|---|---|---|
| Alprenolol (cationic) | $J = 5.36 \times 10^{-7}$ mg/cm$^2$/sec | $J = 7.74 \times 10^{-7}$ | $J = 1.84 \times 10^{-6}$ | $J = 2.10 \times 10^{-6}$ |
| | $P = 5.36 \times 10^{-8}$ | $P = 7.74 \times 10^8$ | $P = 1.84 \times 10^{-7}$ | $P = 2.10 \times 10^{-7}$ |

B. Effect of pH on drug penetration through hairless mouse skin Pretreated with sigma papain of concentration 0.093 mg/ml for 24 hours

| J&P | pH | | | |
|---|---|---|---|---|
| Drug | 5.9 | 6.6 | 7.4 | 8.0 |
| Acetylcholine Chloride | $J = 6.00 \times 10^{-4}$ mg/cm$^2$/sec | $J = 7.77 \times 10^{-4}$ | $J = 6.46 \times 10^{-4}$ | $J = 6.28 \times 10^{-4}$ |
| | $P = 3.00 \times 10^{-6}$ cm/sec | $P = 3.88 \times 10^{-6}$ | $P = 3.23 \times 10^{-6}$ | $P = 3.14 \times 10^{-6}$ |
| | $E = 103.09$ | $E = 149.23$ | $E = 100.94$ | $E = 67.38$ |
| Progesterone | $J = 2.88 \times 10^{-7}$ mg/cm$^2$/sec | $J = 3.51 \times 10^{-7}$ | $J = 2.73 \times 10^{-7}$ | $P = 2.89 \times 10^{-7}$ |
| | $P = 3.60 \times 10^{-6}$ cm/sec | $P = 4.39 \times 10^{-6}$ | $P = 3.41 \times 10^{-6}$ | $P = 3.61 \times 10^{-6}$ |
| | $E = 1.25$ | $E = 1.50$ | $E = 1.17$ | $E = 1.17$ |
| Warfarin | $J = 1.27 \times 10^{-7}$ mg/cm$^2$/sec | $J = 1.20 \times 10^{-7}$ | $J = 0.99 \times 10^{-7}$ | $J = 1.21 \times 10^{-7}$ |
| | $P = 1.27 \times 10^{-6}$ cm/sec | $P = 1.20 \times 10^{-6}$ | $P = 0.99 \times 10^{-6}$ | $P = 1.21 \times 10^{-6}$ |
| | $E = 7.65$ | $E = 13.10$ | $E = 21.15$ | $E = 25.58$ |
| Alprenolol | $J = 1.20 \times 10^{-5}$ mg/cm$^2$/sec | $J = 1.33 \times 10^{-5}$ | $J = 1.32 \times 10^{-5}$ | $J = 1.65 \times 10^{-5}$ |
| | $P = 1.20 \times 10^{-6}$ cm/sec | $P = 1.33 \times 10^{-6}$ | $P = 1.32 \times 10^{-6}$ | $P = 1.65 \times 10^{-6}$ |
| | $E = 22.39$ | $E = 17.18$ | $E = 7.17$ | $E = 7.86$ |

EXAMPLE VI

Fourier Transform Infrared Spectroscopy Studies

A. Comparisons of normal stratum corneum (from mouse skin) to stratum corneum treated with a 0.09% concentration of papain for 24 hours was performed using Fourier Transform Infrared spectroscopy (FTIR). The results showed significant changes occurring in the amide III, beta sheet, and alpha-helix formations of the stratum corneum cells. It is postulated that a shift from a random form of protein to the more organized beta sheet structure occurs. The alpha-helix structures of skin protein could be fractionated, uncoiled, or both. Removal of papain from the mouse showed partial recovery in 24 hours and nearly complete recovery in 48 hours.

FTIR absorbance spectra of pure cast papain showed slight, but significantly different peak positions than papain treated skin and included a peak at 1516 cm$^{-1}$ which did not appear in the treated stratum corneum. This data seems to indicate a complete removal of the papain from the treated stratum corneum, and the FTIR structural data of the skin represent changes only in the protein of the stratum corneum.

A comparison of symmetric and asymmetric CH stretch bands was then made. These two bands represent lipid structure and would show any changes in the stratum corneum lipids caused by the papain. Peak position of these two bands as well as the length of a horizontal line drawn at 70% of peak height showed that there was no change in lipid structure.

B. Azone™ was tested as a permeation enhancer with and without the presence of papain. When papain was present the changes in protein FTIR areas were not significantly different than those observed with papain alone. Azone™ by itself did not change protein FTIR areas. When Azone™ was present it apparently caused a lengthening of both symmetric and asymmetric CH stretch lines but did not change their peak positions.

TABLE I

Comparisons of untreated, papain-treated, Azone™ -treated and papain plus Azone™ -treated stratum corneum ("SC") are shown below as peak positions or as length of the 70% line. Absorbance in protein areas (cm$^{-1}$)

| Untreated | Papain Treated | Azone Treated | Papain plus Azone treated |
|---|---|---|---|
| 1456 | 1464.7 | 1461.8 | 1467.6 |
| 1400.5 | 1403.8 | 1402 | 1408.4 |
| 1244 | 1236.6 | 1244.5 | 1237.4 |
| 1267 | 1263.7 | 1267.4 | 1264 |
| 1295 | 1288.4 | 1296.6 | 1290.4 |

Azone™ by itself did not significantly effect the protein absorbance areas.

TABLE II

Absorbance in lipid areas (cm$^{-6}$)

|  | Untreated | Papain Treated | Azone Treated | Papain plus Azone Treated |
|---|---|---|---|---|
| Symmet CH | 2848.3 | 2848.5 | 2848.3 | 2848.3 |
| Asymmet CH | 2916.5 | 2916.3 | 2916.5 | 2916.5 |

No significant difference in peak positions.

TABLE III

Length of the 70% line in the lipid areas (cm$^{-1}$)

|  | Untreated | Papain Treated | Azone™ Treated | Papain plus Azone treated |
|---|---|---|---|---|
| Symmet CH | 8.6 | 9.1 | 11.4 | 11.4 |
| Asymmet CH | 17.5 | 17.5 | 27.2 | 21.1 |

70% line lengthened when Azone™ was present

TABLE IV

Overall comparisons of FTIR spectra in Amide III region of untreated, papain treated, and papain treated recovered Data reported as cm$^{-1}$.

| Untreated | Papain treat | 24 hr. rec | 48 hr rec | Significance |
|---|---|---|---|---|
| 1244 | 1236 | 1242.4 | 1243.2 | Amide III |
| 1267 | 1262 | 1271.8 | 1268.4 | Shoulder Beta sheet |
| 1295 | 1288 | 1301.7 | 1296.5 | Alpha helix peak |

TABLE V

Lipid Correlation Data for Papain Peak Positions in cm$^{-1}$

|  | Symmetric CH | Asymmetric CH |
|---|---|---|
| Normal SC | 2848.3 | 2916.5 |
| Treated SC | 2848.5 | 2916.3 |
| 48 hr recovery SC | 2849.3 | 2916.5 |

TABLE VI

Length of 70% line in cm$^{-1}$

|  | Asymmetric line | Symmetric line |
|---|---|---|
| Normal SC | 17.5 | 8.6 |
| Treated SC | 17.5 | 9.1 |
| 48 hr recovery SC | 19.3 | 10.5 |

TABLE VII

Data of zone exposed skin in cm$^{-1}$

|  | Symm CH | Asymm CH | Asymm 70% | Symm 70% |
|---|---|---|---|---|
| Azone exp SC | 2848.3 | 2916.5 | 27.2 | 11.4 |
| Azone plus papain exp SC | 2848.3 | 2916.5 | 21.1 | 11.4 |

Peak positions did not change but length of the 70% line did change.

TABLE VII-continued

Data of zone exposed skin in cm$^{-1}$

|  | Symm CH | Asymm CH | Asymm 70% | Symm 70% |
|---|---|---|---|---|
| For Asymmetric CH streach 70% line | | | | |
| Normal SC | | | | 17.5 |
| Azone™ treated SC | | | | 27.2 |
| Azone™ plus papain treated SC | | | | 21.1 |
| For symmetric CH streach 70% line | | | | |
| Normal SC | | | | 8.6 |
| Azone™ treated SC | | | | 11.4 |
| Azone™ plus papain treated SC | | | | 11.4 |

No significant changes occurred in the protein areas when azone was used as the only permeation enhancer.

EXAMPLE VIII

Penetration of Polypeptides Through Pretreated Skin

After papain skin treatment pursuant to Example III.1 above, polypeptides were diffused through the pretreated mouse skin using the same concentration and pH values for each test. Pure buffer solution was also diffused through the pretreated skin of the mouse to determine if any endogenous proteins diffused into the diffusate. This showed that the compounds measured originated only from the polypeptides.

Comparisons of solutions of non-diffused polypeptides, diffused polypeptides and diffused buffer solutions were made using gel electrophoresis. The system used for these determinations was sodium dodecyl sulfate polyacrylamide gel electrophoresis (SDS-PAGE), a procedure well-known in the art. These comparisons determined if fragmentation of the diffused polypeptide molecules occurred.

A series of polypeptides of various molecular weights were studied.

The following peptides were used:

| 1. Bovine albumin | MW | 69,000 |
| 2. Carbonic anhydrase | MW | 29,000 |
| 3. Lysozyme | MW | 14,400 |
| 4. Insulin | MW | 6,000 |

RESULTS

BSA (Bovine Serum Albumin)

The BSA that diffused through the pretreated mouse skin was fractionated to a great extent. The non-diffused BSA showed a distinct stained band within the gel while the diffused BSA showed small extended bands indicating compounds of smaller and varying molecular weights. There were no detectable endogenous compounds that diffused out of the papain-treated skin when buffer solution was used as the only diffusing medium.

Carbonic Anhydrase

This molecule fractionated during the permeation process. Here a comparison of a solution of carbonic anhydrase and the same molecule that remained in the donor solution of the diffusion cell was made to determine if exposure of the molecule to the papain treated skin without diffusion would cause any change in the carbonic anhydrase molecule. There appeared to be no change or breakdown of the molecule due to exposure of the papain treated skin without diffusion.

Lysozyme

Comparisons of solutions of non-diffused lysozyme, non-diffused lysozyme from the donor cell and diffused lysozyme showed no significant difference in molecular size. The molecule remained intact and did not break apart.

Insulin (Regular, Bovine)

Electrophoresis of a solution of insulin and the diffused insulin produced extended stained areas in the gel. It would seem that the electrophoretic process caused considerable agglutination and the determination of molecular fragmentation due to the permeation would be very difficult if not impossible.

The preceding examples are exemplary and are not intended to limit the scope of the appended claims which define the invention.

What is claimed:

1. A method of delivering a drug through the skin of an animal comprising:

applying a percutaneous permeation enhancer to a localized area of the skin of an animal to enhance the permeability of said skin to a drug, said percutaneous permeation enhancer comprising a proteolytic enzymatic component and a non-enzymatic component;

occluding said localized area of skin with occlusion means;

removing said occlusion means; and applying a percutaneously administrable drug to said localized area of skin to effect permeation of said drug through said skin.

2. The method of claim 1 wherein effective amounts of proteolytic enzymatic and non-enzymatic permeation enhancers are in admixture with one another before application to the localized area of the skin.

3. The method according to claim 2 further including the step of occluding said localized area of skin after application of said drug.

4. The method according to claim 2 wherein said percutaneous permeation enhancer is maintained in contact with said localized area of skin for less than 24 hours.

5. The method according to claim 1 wherein said proteolytic enzymatic component includes papain and a buffered saline solution.

6. The method of claim 5 wherein said papain is combined with a chelating agent and cysteine.

7. The method of claim 6 wherein said chelating agent is ethylene diaminetetraacetic acid.

8. The method of claim 5 wherein said papain has a concentration of about 0.019 mg/ml to about 0.093 mg/ml.

9. The method of claim 8 wherein said non-enzymatic component is a lactam compound.

10. The method according to claim 9 wherein said lactam compound is 1-n-Dodecylazacycloheptan-2-one.

11. The method according to claim 9 wherein said lactam compound is a 1-substituted-azacycloheptan-2-one enhancer.

12. The method of claim 8 wherein said non-enzymatic permeation enhancer is a combination of ethyl acetate and ethyl alcohol.

13. The method of claim 8 wherein said non-enzymatic permeation enhancer is ethyl alcohol.

14. The method of claim 8 wherein said non-enzymatic permeation enhancer is dioxolane.

15. The method of claim 8 wherein said non-enzymatic permeation enhancer is a combination of caprylic acid and capric triglyceride.

16. The method of claim 8 wherein said non-enzymatic permeation enhancer is n-decyl methyl sulfoxide.

17. The method of claim 8 wherein said non-enzymatic permeation enhancer is a surfactant.

18. The method according to claim 1 wherein said drug is a quaternary compound.

19. The method according to claim 1 wherein said drug is a polar nonionic chemical.

20. The method according to claim 1 wherein said drug is a nonpolar, nonionic chemical.

21. The method of claim 1 wherein said drug is a polypeptide.

22. The method of claim 21 wherein said polypeptide has a molecular weight less than 15,000.

23. The method according to claim 1 further including substantially removing said percutaneous permeation enhancer from said skin before applying said drug to said localized area of skin.

24. A method of enhancing the permeability of a localized area of skin to a chemical, said method comprising applying a patch to the localized area of skin, said patch comprising a backing and a permeable membrane affixed to said backing forming a space therebetween, said space sized to retain a percutaneous permeation enhancer compound therein to enhance the skin's permeability to the chemical, said percutaneous permeation enhancer comprising a proteolytic enzyme component and a non-enzymatic component.

25. The method of claim 24 wherein said percutaneous permeation enhancer is an admixture of activated papain, propylene glycol, 1-n-dodecylazacyclo-heptan-2-one, surfactant and normal saline.

26. The method of claim 25 wherein said activated papain comprises a mixture of papain, a chelating agent, and cysteine.

27. The method according to claim 1 wherein said non-enzymatic component is applied to said skin followed by application of said enzymatic component prior to said step of applying said occlusion means.

28. The method according to claim 1 wherein said enzymatic component is applied to said skin first followed by application of said non-enzymatic component before applying said occlusion means.

29. The method according to claim 24 wherein said enzyme component and said non-enzyme component of said percutaneous permeation enhancer are mixed with a solvent and injected into said patch immediately prior to application of said patch to said skin.

30. The method according to claim 24 further comprising the step of removing from said skin said patch containing said percutaneous permeation enhancer and applying at least one subsequent patch containing an effective amount of percutaneously deliverable drug to said localized area of skin.

31. A method of delivering a drug through the external tissue of an animal comprising:

applying a percutaneous permeation enhancer to a localized area of modified epidermis of an animal to enhance the permeability of said modified epidermis to a drug, said percutaneous permeation enhancer comprising an enzymatic component and a non-enzymatic component;

occluding said localized area of modified epidermis with occlusion means;

removing said occlusion means; and applying a percutaneously administrable drug to said localized area of modified epidermis to effect permeation of said drug through said modified epidermis.

32. A method of delivering a drug through the skin of an animal comprising:

applying a percutaneous permeation enhancer to a localized area of the skin of an animal to enhance the permeability of said skin to a drug, said percutaneous permeation enhancer comprising an enzymatic component and a non-enzymatic component;

removing any excess amount of said percutaneous permeation enhancer from said localized area of skin; and applying a percutaneously administrable drug to said localized area of skin to effect permeation of said drug through said skin.

* * * * *

UNITED STATES PATENT AND TRADEMARK OFFICE
CERTIFICATE OF CORRECTION

PATENT NO. : 5,534,260
DATED : July 9, 1996
INVENTOR(S) : Petersen et al.

It is certified that error appears in the above-identified patent and that said Letters Patent is hereby corrected as shown below:

In Column 13, line 14, change "$P=7.74 \times 10^8$" to --$P=7.74 \times 10^{-8}$--; and In Column 13, line 12, below "$P=5.36 \times 10^{-8}$" insert --cm/sec--.

Signed and Sealed this

Nineteenth Day of May, 1998

Attest:

BRUCE LEHMAN

Attesting Officer    Commissioner of Patents and Trademarks